United States Patent [19]

Skeirik

[11] 4,084,320
[45] Apr. 18, 1978

[54] SYSTEM FOR MIXING AND DISPENSING DENTAL AMALGAM

[76] Inventor: Lewis Skeirik, 24 Central St., Georgetown, Mass. 01833

[21] Appl. No.: 707,296

[22] Filed: Jul. 21, 1976

[51] Int. Cl.² ............................................. A61C 5/04
[52] U.S. Cl. ...................................................... 32/60
[58] Field of Search ................................. 32/40 A, 60; 254/DIG. 20; 222/144, 144.5, 145

[56] References Cited

U.S. PATENT DOCUMENTS 3,222,037  12/1965  Thiel et al. .......................... 32/40 A

FOREIGN PATENT DOCUMENTS 2,024,331  5/1970  Germany .............................. 32/40 A Primary Examiner—Robert Peshock Attorney, Agent, or Firm—Morse, Altman, Oates & Bello

[57] ABSTRACT

A capsule is provided in which dental amalgam may be mixed, and the capsule itself connected to a dispenser for direct application into a cavity. The capsule includes a cylindrical body with a longitudinal offset passage holding a quantity of silver fillings or the like. End caps are removably mounted to each end of the body portion, with one cap formed with a socket having a pestle adapted to move in and out of the passage, while the other cap is provided with a pair of sockets, one with a pestle and one with a charge of mercury. The second cap is rotatable to different stop positions, first to align the cavity with the mercury to mix it with the silver and then to align the pestle cavity with the passage for mixing. The dispenser includes a detachable nozzle tip and a plunger engageable at opposite ends of the center portion for dispensing the mixed amalgam.

10 Claims, 8 Drawing Figures

U.S. Patent        April 18, 1978        4,084,320
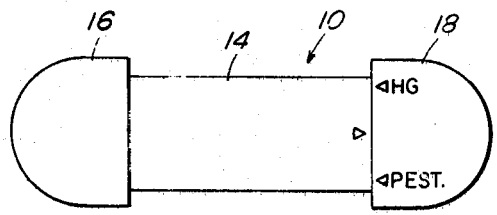
FIG. 1
FIG. 2
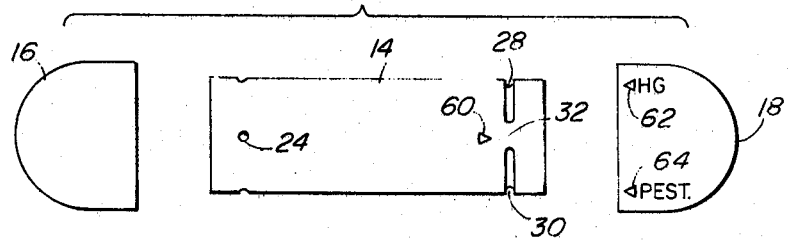
FIG. 3
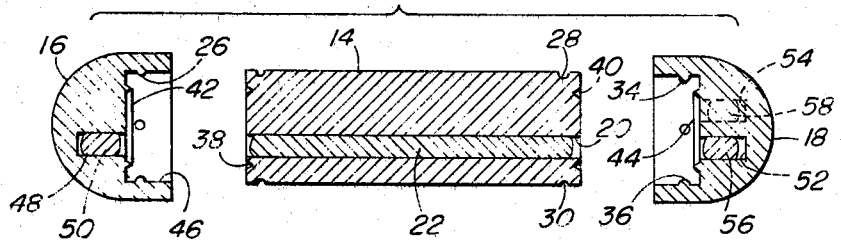
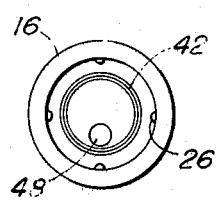 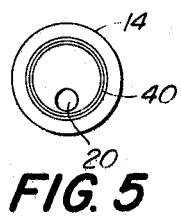 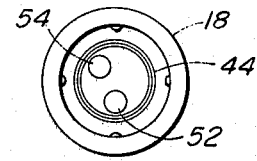
FIG. 4      FIG. 5      FIG. 6
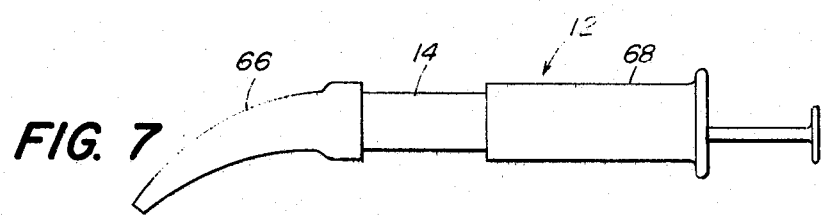
FIG. 7
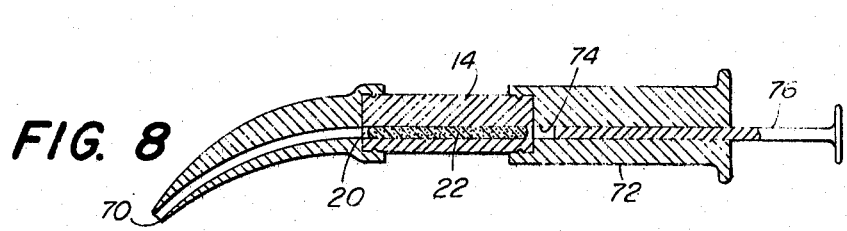
FIG. 8

4,084,320

SYSTEM FOR MIXING AND DISPENSING DENTAL AMALGAM

BACKGROUND OF THE INVENTION

1. Field of the Invention

This invention relates generally to dental equipment and more particularly is directed towards a system for mixing and dispensing dental amalgam including a capsule for mixing dental amalgam and a dispenser to which the capsule is connected for direct discharge of the amalgam.

2. Description of the Prior Art

In dental practice cavities commonly are filled, after initial preparation by drilling, with silver amalgam. Typically, the amalgam is provided in a capsule in which silver powder is isolated at one end and a small quantity of mercury at the other end. When the amalgam is to be prepared, the mercury is released into the silver powder by pulling up on one end of the capsule which is designed to release the mercury into the body of the capsule. The capsule is then placed in a mechanical vibrator and the silver and mercury are mixed to form the amalgam. A pestle may be provided to enhance the mixing action. Once the amalgam is mixed, the capsule is opened and the amalgam placed on a working surface for transfer to the cavity by means of an instrument known as an amalgam carrier, which has a hollow cylinder at one end and a finger actuated lever. The hollow cylinder is packed with the amalgam, carried to the tooth and the lever depressed to discharge the amalgam into the cavity. The process is quite slow and normally requires the services of a dental assistant to continually load the carrier and hand it to the dentist who condenses the silver in the cavity.

It is an object of the present invention to provide improvements in dental mixing capsules and dispensers. Another object of this invention is to provide a cavity filling system comprised of a combination dental amalgam mixing capsule and a dispenser to which the capsule may be connected for direct discharge of the amalgam into the filling.

SUMMARY OF THE INVENTION

This invention features a system for mixing and dispensing dental amalgam comprising a capsule in which the amalgam is mixed and a dispenser to which the capsule is connected for delivery of the amalgam to the cavity. The capsule includes a cylindrical body portion having removable end caps, with the body portion formed with a longitudinal offset passage filled with silver powder or the like. One cap is formed with a socket in which is mounted a pestle, while the other end cap is formed with two sockets and is rotatable with respect to the body portion. The second cap sockets carry a pestle in one and a charge of mercury in the other. The mercury is mixed with the silver by twisting the second cap first to one position and then to a second position to align the pestle with the body passage. Once the amalgam has been mixed it is connected to the dispenser which includes a plunger and a nozzle tip by means of which the amalgam is discharged.

BRIEF DESCRIPTION OF THE DRAWINGS

FIG. 1 is a view in side elevation of a dental mixing capsule made according to the invention.

FIG. 2 is an exploded view in side elevation of the FIG. 1 capsule,

FIG. 3 is an exploded sectional view in side elevation of the mixing capsule,

FIG. 4 is an end elevation of the left-hand cap of FIG. 3,

FIG. 5 is an end elevation of the body portion,

FIG. 6 is an end elevation of the right-hand cap of FIG. 3,

FIG. 7 is a view in side elevation of the mixing capsule and dispensing instrument, and FIG. 8 is a sectional view in side elevation of the FIG. 7 assembly.

DETAILED DESCRIPTION OF THE PREFERRED EMBODIMENTS

Referring now to the drawings, the reference character 10 generally indicates a dental mixing capsule for use with a dispensing device 12 from which mixed dental amalgam may be delivered directly to a cavity. The capsule 10 is comprised of a cylindrical body portion 14 and a pair of detachable end caps 16 and 18. The body portion 14 is formed with a longitudinal passage 20 that is offset with respect to the center line of the body portion and is adapted to contain a quantity of silver powder or fillings 22. The body portion may be fabricated from many suitable materials, and a moldable plastic, such as polyethylene, PVC, or the like, may be used to advantage.

The left-hand end of the body portion is formed on its outer surface with a series of indents 24 which lockably engage with cooperating detents 26 formed on an opposing inner annular face of the end cap 16. The right-hand end of the body portion is formed with a pair of annular grooves 28 and 30 separated by means of a fillet 32 forming a shoulder stop for reasons that will presently appear. The grooves 28 and 30 are adapted to slidably engage with a pair of detents 34 and 36 formed on an opposing inner annular face of the end cap 18. Each end of the body portion may also be formed with an annular groove 38 and 40 to provide a sealing engagement with a cooperating V-rib 42 and 44, respectively, formed on the inner faces of the end caps 16 and 18, as best shown in FIGS. 3, 4 and 6.

The end cap 16 is formed with a concentric recess 46 adapted to receive the left-hand end portion of the body 14 and dimensioned to provide a snug fit therewith. The end cap 16 may also be fabricated from a molded plastic material, and both the body portion as well as the end cap provide sufficient resiliency so as to allow the detents 26 to snap over into locking engagement with the indents 24. Once in position the end cap may not be rotated and the rib 42 will seat in the groove 38 to provide a tight seal for the assembled capsule. The end cap is also formed with a socket 48 in which is mounted a pestle 50. The socket is offset with respect to the center line of the cap and aligns with the passage 20. The pestle is preferably of a relatively heavy metal and facilitates mixing of the amalgam when the capsule is subsequently placed in a mechanical vibrator. The entry of the passage 20 may be slightly chamfered to facilitate movement of the pestle in and out of the passage.

The right-hand end cap 18 is of a configuration somewhat similar to the end cap 16, with the exception that it is formed with a pair of sockets 52 and 54, both offset from the center line and both adapted to be aligned sequentially with the passage 20 by rotating the cap from one position to another. The socket 52 is provided with a pestle 56 while the socket 54 contains a quantity of mercury 58. The detents 34 and 36, which ride in the grooves 28 and 30, permit limited rotation of the end cap 18 by virtue of the shoulder stops formed by the fillet 32. Thus, the cap may be twisted from one stop position to another. In one stop position the socket 54 will align with the passage 20 to allow the mercury 54 to drop into the passage 20 and combine with the silver 22. In practice, the capsule should be tapped against a hard surface to insure that the mercury drops down into the passage. Once the mercury is in the passage, the cap is then twisted to the next stop position to align the socket 52 with the passage 20 so that the pestle 56 may be brought to bear. Again, the right-hand entry to the passage 20 may be chamfered to guide the pestle into the passage.

In order to insure that the dentist or his assistant is aware of the position of the cap with respect to the body portion, appropriate indicia 60, 62 and 64 may be provided on the body portion as well as on the cap 18 as suggested in FIGS. 1 and 2. The indicia will indicate that, when aligned, the appropriate cap socket is aligned with the body passage 20.

Once the mercury has been introduced to the silver and the cap 18 has been twisted so that the pestle 56 is in position for use, the capsule is placed in a mechanical vibrator for a time sufficient to thoroughly mix the amalgam. Once the mixing is complete, the end caps are snapped off and the body portion 14 is connected to the dispenser 12. The dispenser 12 includes a detachable nozzle tip 66 and a gun portion 68. The tip 66 typically is in the form of a slightly curved, tapered nozzle having an internal passage 70 extending from one end to another and through which the amalgam is delivered to the cavity. The tip generally narrows in the manner illustrated, while the opposite end is dimensioned and configured to snap over the end of the capsule in much the same fashion as the end caps 16 and 18. Similarly the gun portion 68 is recessed at its left-hand end to detachably lock with the right-hand end of the cap in the manner shown. The gun portion includes a housing 72 formed with a longitudinal passage 74 in which is mounted a plunger 76 which aligns with the passage 20 of the capsule body portion 14. In practice, if one or both of the pestles remain in the passage 20 of the body portion the foremost one may be removed by pressing the plunger of the dispenser until the pestle is forced out through the nozzle tip. The second pestle will remain either in the capsule or in the nozzle.

The system is quick, simple and efficient, and since the amalgam is kept in a closed capsule, except when the caps are removed, the doctor, his assistant and the patient are not exposed unduly to mercury vapors.

While the invention has been described with particular reference to the illustrated embodiment, numerous modifications thereto will appear to those skilled in the art.

Having thus described the invention, what I claim and desire to obtain by Letters Patent of the United States is:

1. A system for mixing and dispensing dental amalgam, comprising
 (a) a capsule adapted to contain constituents for said amalgam, and
 (b) a dispenser operatively connectable to said capsule and adapted to discharge said amalgam from said capsule,
 (c) said capsule being formed with separate chambers for separately storing said constituents and means for connecting said chambers for mixing said constituents,
 (d) said capsule including a body portion formed with a through passage adapted to contain one of said constituents and at least one cap formed with a cavity adapted to contain another of said constituents,
 (e) said cap being movably connected to said body portion whereby said cavity may be moved from a misaligned position to an aligned position with respect to said passage.

2. A system, according to claim 1, wherein said body portion is cylindrical and a cap is detachably connected to each end thereof.

3. A system according to claim 2, wherein said passage extends parallel to the axis of said body portion and offset from the centerline thereof.

4. A system, according to claim 3, wherein said one cap is rotatably connected to said body portion.

5. A system, according to claim 4, wherein said one cap is formed with a pair of cavities, one of said cavities adapted to contain said other constituent and a pestle mounted movably in the other of said cavities, either of said cavities adapted to be aligned with said passage by rotation of said one cap.

6. A system, according to claim 5, wherein said other cap is formed with a cavity aligned with said passage and a pestle movably mounted therein.

7. A system, according to claim 4, wherein said body portion and said one cap are formed with cooperating stop means for limiting the rotation of said one cap whereby said cavities may be selectively aligned with said passage by rotating said cap into stop positions.

8. A system, according to claim 1, wherein said dispenser includes a gun, said gun including a plunger in alignment with said passage when said capsule is connected to said dispenser for forcing said amalgam from said passage.

9. A system, according to claim 8, wherein said dispenser includes a nozzle tip detachably connected to said capsule in register with said passage.

10. A capsule for dental amalgam comprising
 (a) a body portion formed with an off-center passage therethrough from end to end of said body portion and adapted to contain one amalgam constituent,
 (b) a cap detachably mounted to each end of said body portion,
 (c) at least one of said caps being formed with at least a pair of off-center cavities adapted to contain a pestle in one cavity and another amalgam constituent in the other cavity,
 (d) said one cap being rotatably connected to said body portion whereby either of said cavities may be aligned with said passage by selective rotation of said one cap.

* * * * *